US011813372B2

(12) United States Patent
Oda et al.

(10) Patent No.: US 11,813,372 B2
(45) Date of Patent: Nov. 14, 2023

(54) LIGHT SOURCE DEVICE, AND STERILIZING/DEODORIZING DEVICE

(71) Applicant: Ushio Denki Kabushiki Kaisha, Tokyo (JP)

(72) Inventors: Koji Oda, Tokyo (JP); Junya Asayama, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 195 days.

(21) Appl. No.: 17/472,217

(22) Filed: Sep. 10, 2021

(65) Prior Publication Data

US 2022/0072168 A1     Mar. 10, 2022

(30) Foreign Application Priority Data

Sep. 10, 2020     (JP) .................................. 2020-151848

(51) Int. Cl.
  *A61L 2/10*     (2006.01)
  *H05B 41/28*    (2006.01)
  *H05B 41/38*    (2006.01)

(52) U.S. Cl.
  CPC .............. *A61L 2/10* (2013.01); *H05B 41/28* (2013.01); *H05B 41/38* (2013.01); *A61L 2202/11* (2013.01); *A61L 2202/14* (2013.01)

(58) Field of Classification Search
  CPC .... A61L 2/10; A61L 2202/11; A61L 2202/14; A61L 2/24; A61L 9/20; H05B 41/28;
  (Continued)

(56) References Cited

U.S. PATENT DOCUMENTS 6,858,988 B1 * 2/2005 Laroussi ............... H01J 65/046
                                                315/111.21
2001/0013759 A1    8/2001 Thiel et al.
(Continued)

FOREIGN PATENT DOCUMENTS

JP     2001-257093 A    9/2001
JP     2002-319371 A   10/2002
(Continued)

OTHER PUBLICATIONS

Translation of JP-2020047527-A; Ishikawa T; Mar. 2020 (Year: 2020).*
(Continued)

*Primary Examiner* — Renan Luque
(74) *Attorney, Agent, or Firm* — Studebaker & Brackett PC

(57) ABSTRACT

Provided is a new light source device using an excimer lamp, particularly, a light source device for sterilization and deodorization. The light source device includes an excimer lamp and a flyback-type lighting device that supplies power to the excimer lamp. The lighting device includes a transformer, a switching element, and a control circuit that supplies a drive signal to the switching element. The control circuit controls the switching element on and off so that the switching frequency (FS) for the switching element at the time of starting to light is lower than the switching frequency (FO) at the time of steady-state lighting, and the ON-duty (TS) for the switching element at the time of starting to light is lower than the ON-duty (TO) at the time of steady-state lighting.

7 Claims, 4 Drawing Sheets

(58) Field of Classification Search
CPC .. H05B 41/38; H05B 41/2806; H05B 41/382; H05B 41/04; Y02B 20/00
See application file for complete search history.

(56) References Cited

U.S. PATENT DOCUMENTS

| | | | |
|---|---|---|---|
| 2007/0228992 | A1 | 10/2007 | Matsumoto |
| 2012/0194070 | A1* | 8/2012 | Tao .................. H05B 41/24 315/34 |
| 2021/0009416 | A1 | 1/2021 | Mamura et al. |

FOREIGN PATENT DOCUMENTS

| | | | | |
|---|---|---|---|---|
| JP | 2009-123406 | A | | 6/2009 |
| JP | 2020-011856 | A | | 1/2020 |
| JP | 2020-047527 | A | | 3/2020 |
| JP | 2020047527 | A | * | 3/2020 ............ H05B 41/14 |
| JP | 6717335 | B2 | | 7/2020 |

OTHER PUBLICATIONS

The extended European search report issued by the European Patent Office dated Jan. 18, 2022, which corresponds to European Patent Application No. 21195880.6-1202 and is related to U.S. Appl. No. 17/472,217.

International Search Report and Written Opinion of the International Searching Authority; dated Nov. 9, 2021 in PCT/JP2021/032868.

Communication pursuant to Article 94(3) EPC issued by the European Patent Office dated Jan. 3, 2023, which corresponds to European Patent Application No. 21195880.6-1201 and is related to U.S. Appl. No. 17/472,217.

An Office Action; "Notice of Reasons for Refusal," mailed by the Japanese Patent Office dated Jun. 1, 2023, which corresponds to Japanese Patent Application No. 2022-547605 and is related to U.S. Appl. No. 17/472,217; with English language translation.

* cited by examiner

LIGHT SOURCE DEVICE, AND STERILIZING/DEODORIZING DEVICE

BACKGROUND OF THE INVENTION

Field of the Invention

The present invention relates to a light source device. In particular, the present invention relates to a light source device including an excimer lamp that emits ultraviolet light by dielectric-barrier discharge and a lighting device of the excimer lamp.

Description of the Related Art

In recent years, a sterilizing/deodorizing device using an excimer lamp that emits ultraviolet light by dielectric-barrier discharge has been known. This excimer lamp generates a so-called dielectric-barrier discharge by a pair of electrodes arranged with a light-emitting tube made of dielectric material interposed therebetween and excites a discharge gas enclosed inside to emit ultraviolet light. For example, in the case of enclosing xenon gas as the discharge gas, vacuum ultraviolet light having a single peak at a wavelength of 172 nm is generated.

In recent years, the application of this type of excimer lamp to be mounted on a vehicle or a lighting fixture has been attracting attention, and device development corresponding to such application is strongly required as a light source device.

PRIOR ART DOCUMENT

Patent Document

Patent Document 1: JP 6717335 B2

SUMMARY OF THE INVENTION

Therefore, an object of the present invention is to provide a new light source device using an excimer lamp, particularly a light source device for sterilization/deodorization.

To solve the above problem, a light source device according to the present invention includes an excimer lamp that emits ultraviolet light by dielectric-barrier discharge and a flyback-type lighting device that supplies power to the excimer lamp. The lighting device includes a switching element, a transformer to which the switching element is connected on the primary side and the excimer lamp is connected on the secondary side, and a control circuit that supplies a drive signal to the switching element. The control circuit controls the switching element on and off so that the switching frequency (FS) (ON-timing frequency) for the switching element at the time of starting to light the excimer lamp is lower than the switching frequency (FO) for the switching element at the time of steady-state lighting of the excimer lamp, and the ON-duty (TS) for the switching element at the time of starting to light the excimer lamp is lower than the ON-duty (TO) for the switching element at the time of steady-state lighting of the excimer lamp.

Further, the control circuit may control the switching element on and off so that the switching frequency (FS) at the time of starting to light the excimer lamp increases stepwise toward the switching frequency (FO) at the time of steady-state lighting of the excimer lamp.

Further, the control circuit may control the switching elements on and off so that the ON-duty (TS) at the time of starting to light the excimer lamp increases stepwise toward the ON-duty (TO) at the time of steady-state lighting of the excimer lamp.

Further, the excimer lamp may include a light-emitting tube with a substantial rod shape and a pair of electrodes arranged in a ring shape at both ends of the light-emitting tube.

Further, the excimer lamp may emit ultraviolet light having a wavelength of 172 nm.

Further, the excimer lamp may comprise a light-emitting tube with a total length of 10 cm or less, and be a sterilizing/deodorizing lamp used in an enclosed space.

Furthermore, a sterilizing/deodorizing device according to the present invention includes an excimer lamp that emits ultraviolet light by dielectric-barrier discharge; a flyback-type lighting device that supplies power to the excimer lamp; and a control circuit equipped with the lighting device, including a switching element and a transformer to which the switching element is connected on the primary side and the excimer lamp is connected on the secondary side, and which supplies a drive signal to the switching element. The control circuit controls the switching element on and off so that the switching frequency (FS) (ON-timing frequency) for the switching element at the time of starting to light the excimer lamp is lower than the switching frequency (FO) for the switching element at the time of steady-state lighting of the excimer lamp, and the ON-duty (TS) for the switching element at the time of starting to light the excimer lamp is lower than the ON-duty (TO) for the switching element at the time of steady-state lighting of the excimer lamp.

The light source device of the present invention can reliably light the excimer lamp at the time of starting to light, by controlling it differently from the time of steady lighting.

DETAILED DESCRIPTION OF THE PREFERRED EMBODIMENTS

Figure 1:
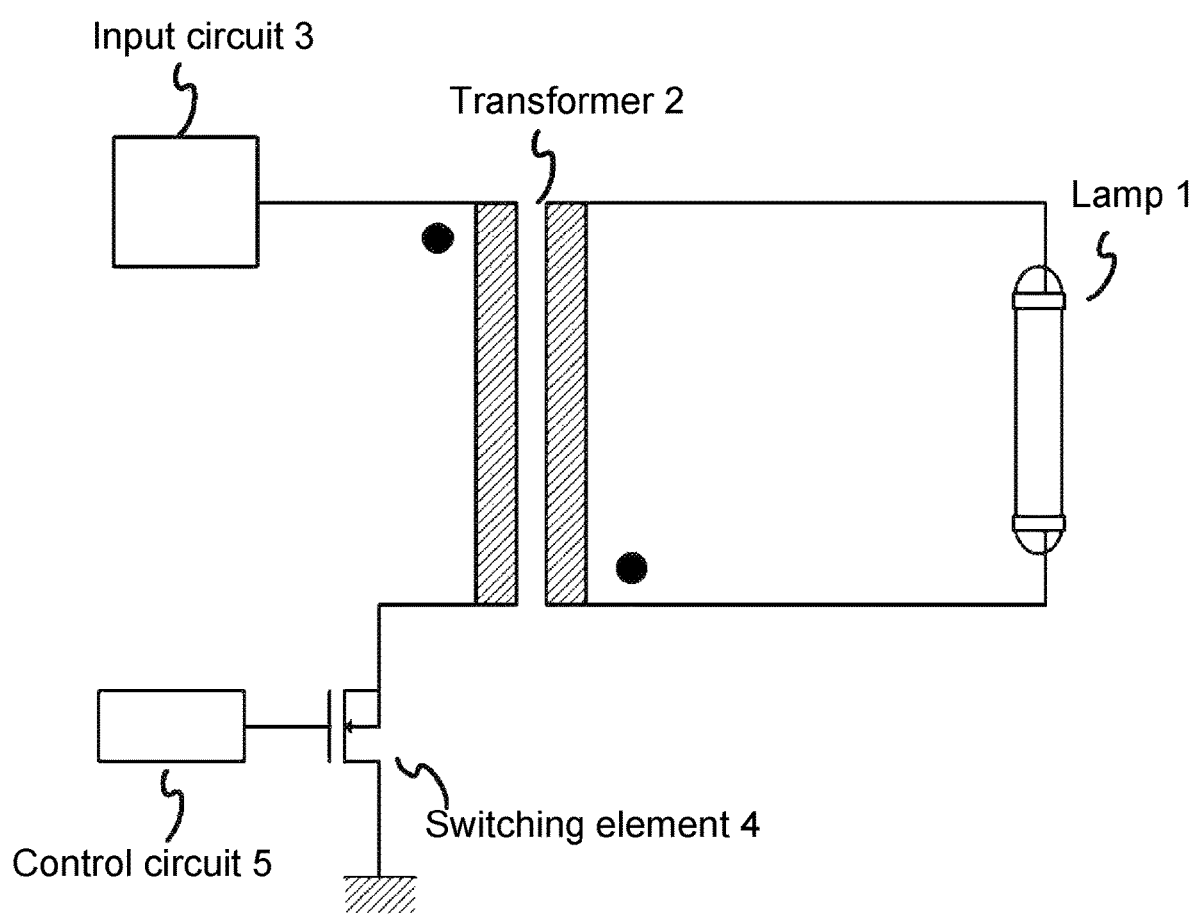
FIG. 1 illustrates an overall configuration of a light source device according to the present invention.

FIG. 1 illustrates an overall configuration of a light source device according to the present invention. The light source device shown in FIG. 1 is equipped with an excimer lamp 1, a transformer 2, an input circuit 3, a switching element 4, and a control circuit 5. The excimer lamp 1 (hereinafter referred to simply as "lamp 1") is equipped with a pair of electrodes, both of which are electrically connected to a secondary winding of the transformer 2. The input circuit 3 to which power is supplied from a commercial power supply or a DC power supply is connected to one end of a primary winding of the transformer 2. The switching element 4 such as a field-effect transistor (FET) element is connected to the other end of the primary winding of the transformer 2, and a control circuit 5 is connected to a gate of the switching element 4. This circuit shown in FIG. 1 is generally called a boost flyback circuit, where a one-pulse voltage waveform is periodically and repeatedly generated on the secondary side of the transformer 2 corresponding to an OFF timing of the switching element 4.

Figure 2A:
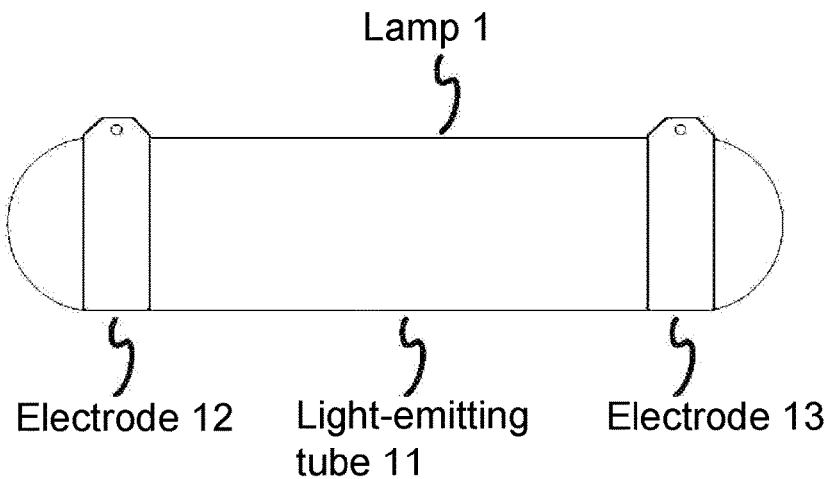
FIGS. 2A and 2B illustrate enlarged views of an excimer lamp according to the present invention.
Figure 2B:
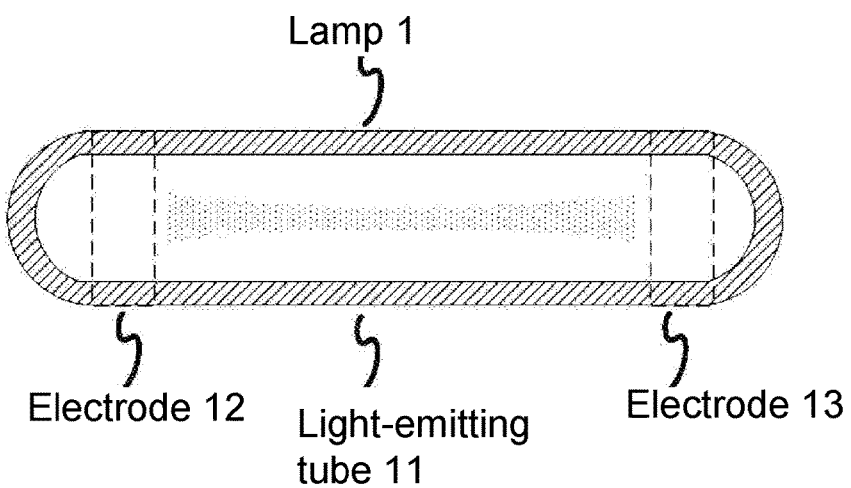

FIGS. 2A and 2B illustrate enlarged views of the lamp 1 according to the present invention. FIG. 2A illustrates an external view of the lamp 1, and FIG. 2B illustrates an internal structure of the lamp 1. The lamp 1 includes a light-emitting tube 11 with a substantial rod shape as a whole, and a pair of electrodes 12 and 13 are provided at both ends thereof. The light-emitting tube 11 is made of quartz glass which is a dielectric material, and xenon gas is sealed therein as a discharge gas. When a voltage is applied to both electrodes, an electrical discharge occurs inside the light-emitting tube 11 as shown in FIG. 2B. This discharge excites the enclosed gas to enter an excimer state, generating vacuum ultraviolet light with a wavelength of 172 nm, for example. Although not illustrated, a platinum paste is applied to the inner surface of the light-emitting tube 11 as a start-up auxiliary function member at the position corresponding to the electrode 12. FIG. 2B schematically illustrates the situation where discharge is occurring in the light-emitting tube 11 with thin hatched notation.

The electrode form of the pair of electrodes 12 and 13 is not limited to the structure shown in FIGS. 2A and 2A. For example, a pair of electrodes with a long strip may be arranged on the outer surface of the light-emitting tube, extending in the longitudinal direction (for example, JP 2009-123406 A), or only one electrode may be arranged inside the light-emitting tube (for example, JP 2002-319371 A).

In the case of using the light source device according to the present invention as a sterilizing/deodorizing device, the lamp 1 is a lamp that emits UVC light (wavelength of 200 to 280 nm) or vacuum-ultraviolet light (wavelength of 200 nm or less). In the case of enclosing krypton (Kr) and bromine (Br) as light-emitting gases, an emission spectrum with a single peak at a wavelength of 207 nm is emitted from krypton bromide excimer molecules (KrBr*), and in the case of enclosing Kr and chlorine (Cl), an emission spectrum with a single peak at a wavelength of 222 nm is emitted from krypton chloride excimer molecules (KrCl*). The lamp 1 according to the present invention is also expected to be mounted on a vehicle or a lighting fixture, in which case the rod-shaped light-emitting tube is relatively short. As a numerical example, the light-emitting tube 11 has a total length of 40 mm and a diameter φ of 6 mm.

Figure 3:
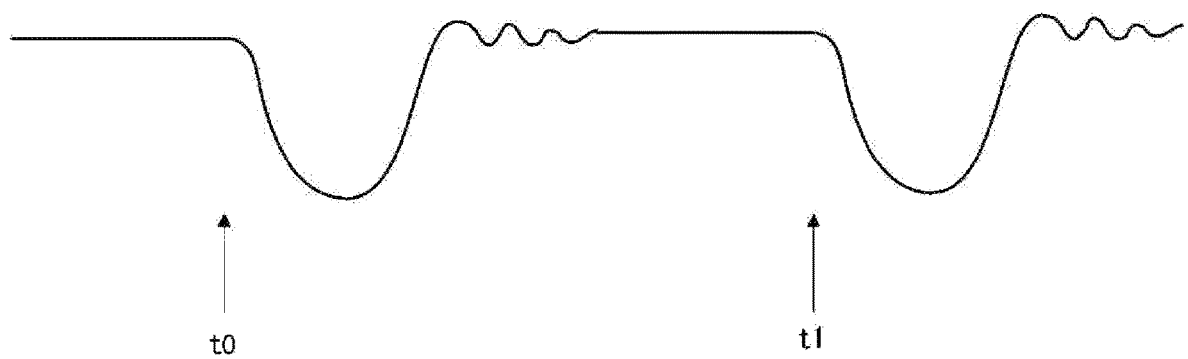
FIG. 3 illustrates a waveform of a voltage applied to a lamp of the light source device according to the present invention.

FIG. 3 illustrates a voltage waveform generated on the secondary side of the transformer 2 in the light source device according to the present invention.

At a moment (t0) when the switching element 4 constituting the flyback circuit is turned off, a voltage of one pulse is generated in the secondary winding of the transformer 2. When the switching element 4 is turned off at the next timing (t1), a similar voltage waveform is repeatedly generated.

Here, although most excimer lamp lighting devices generally supply sine waves or rectangular pulses to the lamp, in the present invention, the flyback circuit shown in FIG. 1 supplies a voltage waveform with a substantially single peak to the lamp 1, as shown in FIG. 3. The oscillation current after the peak hardly occurs in relation to a regenerative current of the FET element (the switching element 4). A conventional excimer lamp is generally large, with a total length of 100 mm or more, and in order to favorably generate a discharge between the electrodes, relatively high voltage sinusoidal or square wave pulses are supplied to the excimer lamp. On the other hand, the light source device according to the present invention is supposed to be mounted on a vehicle or a lighting fixture as one of its applications, in which case the overall scale of the light source device is smaller. In this case, the lamp 1 shown in each of FIGS. 2A and 2B is comparatively small, with a total length of less than 100 mm, which means that a flyback-type lighting circuit suitable for low power and high voltage can be adopted. If the flyback method is adopted for an excimer lamp that requires high power, the transformer of the lighting device will be huge and the switching element will need to be able to withstand high current and high voltage, which is not realistic.

Figure 4:
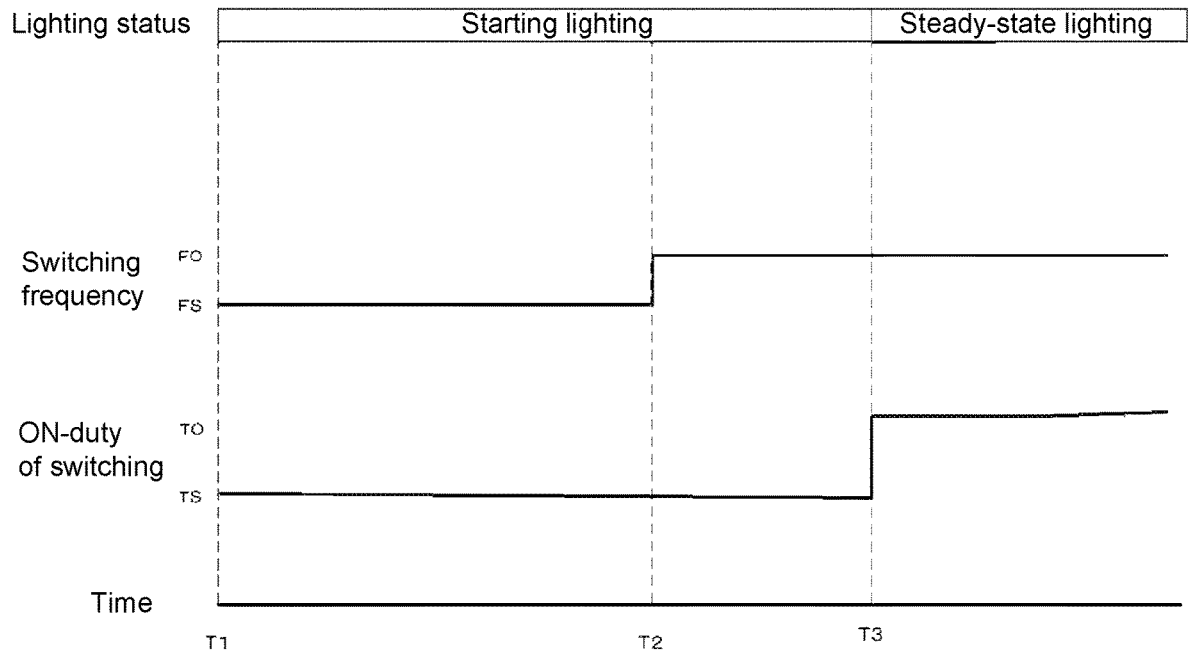
FIG. 4 is a time chart illustrating control contents of the light source device according to the present invention.

FIG. 4 illustrates a time chart for explaining control contents for stably lighting the lamp 1 according to the present invention. At time T1, the excimer lamp is turned on. From time T1 to time T3, the lamp 1 is in a starting lighting state, and after time T3, it is in a steady lighting state.

A switching frequency (FS) from time T2 to time T3 is set to a lower value than a switching frequency (FO) during steady-state lighting. The switching frequency corresponds to a frequency of a signal from the control circuit 5 to the switching element 4 in FIG. 1, but can also be said to be a cycle of a current waveform supplied to the lamp in FIG. 3. The switching frequency may also be described as the ON-timing frequency.

Furthermore, an ON-duty (TS) of switching from time T1 to time T3 is set to a lower value than an ON-duty (TO) during steady-state lighting.

The reason for this is to keep the lamp power almost the same during steady-state lighting as well as during starting lighting. In other words, when the lamp 1 is started lighting, the lighting frequency is lowered and the voltage supplied to the lamp 1 is increased to ensure stable lighting. On the other hand, when the lamp power becomes higher, the ON-duty of the switching element 4 is lowered because the amount of ozone generated increases with the increase in the amount of ultraviolet light.

A numerical example is as follows. The lamp voltage during steady-state lighting is 3.8 kV, while the lamp voltage during starting lighting is 4.5 kV. The switching frequency (FO) during steady-state lighting is 28 kHz while the switching frequency (FS) during starting lighting is 24 kHz. The ON-duty (TO) of the switching element 4 during steady-state lighting is 80%, while the ON-duty (TS) of the switching element 4 during starting lighting is 53%. The timing (elapsed time from time T1 to time T2) for switching the switching frequency from the value at starting lighting (FS) to the value at the steady-state lighting (FO) is 10 ms, and the timing (elapsed time from time T1 to time T3) for switching the ON-duty of the switching element 4 from the value at starting lighting (TS) to the value at the steady-state lighting (TO) is 18 ms.

As described above, although the light source device according to the present invention is downsized, lighting can be stably started and the problem of generating a large amount of ozone due to the increase in the amount of ultraviolet light when starting to light the lamp 1 can be avoided.

Figure 5:
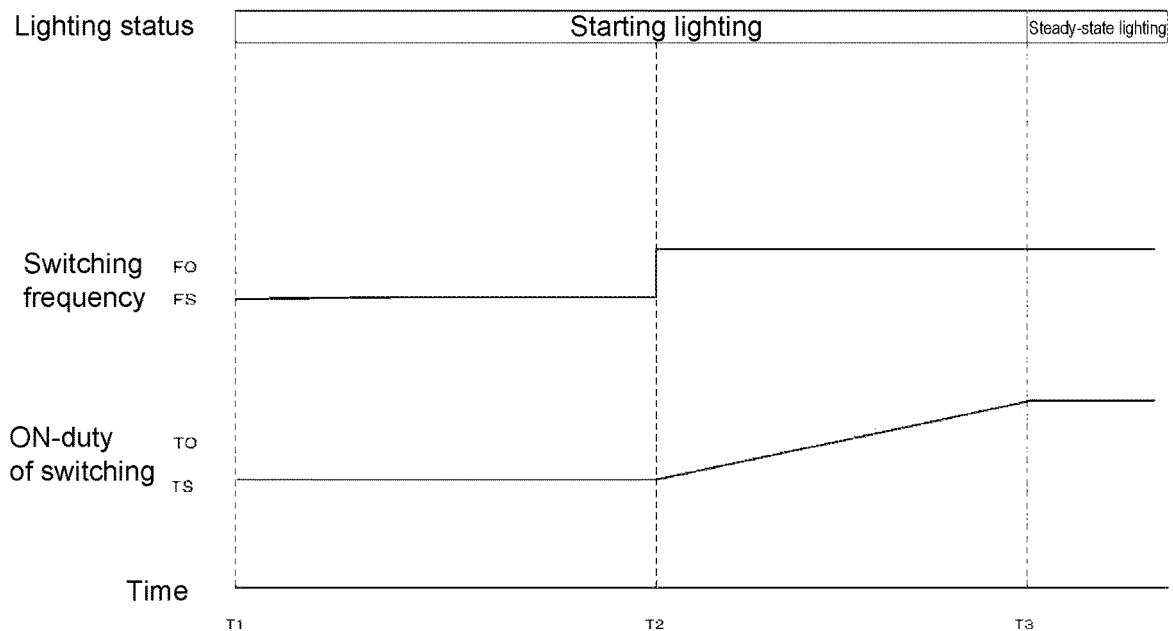
FIG. 5 is a time chart illustrating control contents of the light source device according to the present invention.

FIG. 5 is a modification of FIG. 4 and illustrates a time chart for explaining control contents for stably lighting the excimer lamp according to the present invention.

At time T1, the excimer lamp is turned on. From time T1 to time T3, the lamp 1 is in the starting lighting state, and after time T3, it is in the steady lighting state.

The difference between the control shown in FIG. 5 and the control shown in FIG. 4 is that the ON-duty of the switching element 4 is controlled to increase gradually at the timing (T2) when the switching frequency is switched from the setting value (FS) during lighting starting to the setting value (FO) during steady-state lighting.

In this way, by avoiding a sudden change in the ON-duty of the switching element 4, the amount of change in the ultraviolet light during the transition of the lamp 1 from the starting lighting state to the steady lighting state can be reduced.

Figure 6:
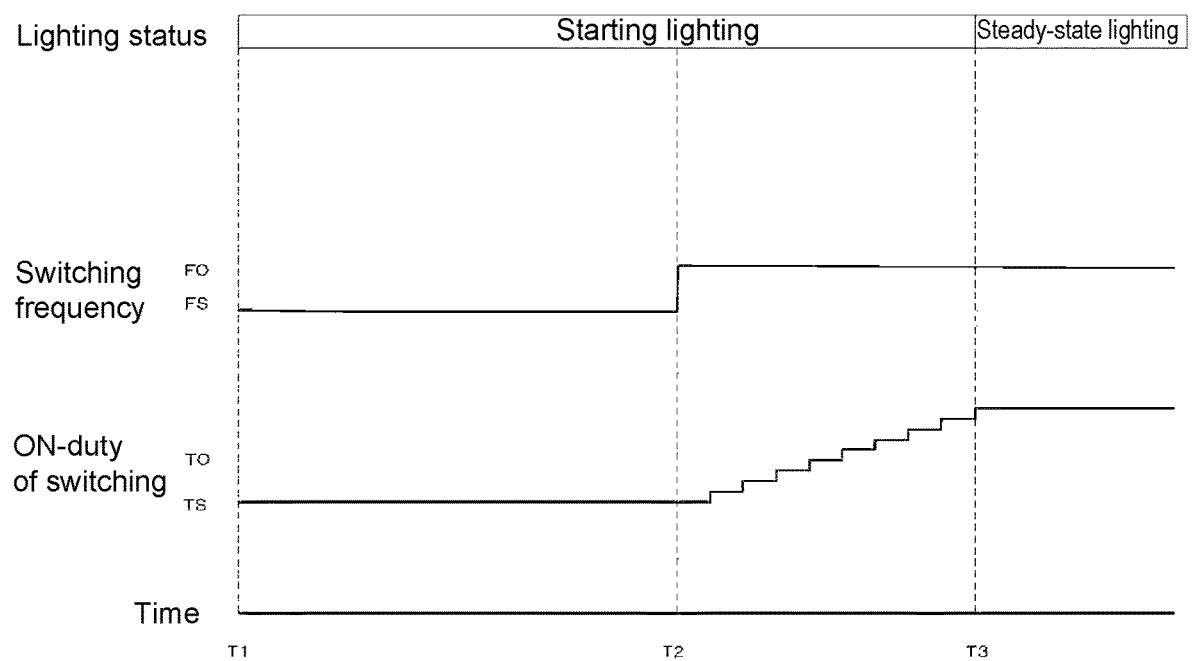
FIG. 6 is a time chart illustrating control contents of the light source device according to the present invention.

FIG. 6 is a further modification of FIGS. 4 and 5 and illustrates a time chart for explaining control contents for stably lighting the lamp 1 according to the present invention.

At time T1, the excimer lamp is turned on. From time T1 to time T3, the lamp 1 is in the starting lighting state, and after time T3, it is in the steady lighting state.

The difference between the control shown in FIG. 6 and the control shown in FIG. 4 is that the ON-duty of the switching element 4 is controlled to increase stepwise at the timing (T2) when the switching frequency is switched from the setting value (FS) during lighting starting to the setting value (FO) during steady-state lighting.

The numerical example shows that the ON-duty of switching element 4 at time T2 is 53%, and the ON-duty is increased in steps of 56%⇒59%⇒62%⇒65%⇒68%⇒71%⇒74%⇒77%⇒80% every 1 millisecond until the ON-duty at steady-state lighting of 80% is reached over 9 milliseconds.

In this way, by avoiding sudden changes in the ON-duty of the switching element 4, the lamp 1 can be stably transitioned from the starting lighting state to the steady lighting state.

What is claimed is:

1. A light source device comprising:
   an excimer lamp that emits ultraviolet light by dielectric-barrier discharge;
   a flyback-type lighting device that supplies power to the excimer lamp;
   a switching element equipped in the lighting device;
   a transformer to which the switching element is connected on the primary side and the excimer lamp is connected on the secondary side, the transformer being equipped in the lighting device; and
   a control circuit that supplies a drive signal to the switching element and that is equipped in the lighting device; wherein
   the control circuit controls the switching element on and off with the switching frequency fixed to the frequency FS and with the ON duty fixed to the ON duty TS for a predetermined time during the time of starting to light the excimer lamp,
   after the predetermined time elapsed, the control circuit controls the switching element on and off with the switching frequency increased from the frequency FS and the ON duty increased from the ON duty TS, and
   the control circuit controls the switching element on and off with the switching frequency fixed to the frequency FO higher than the frequency FS and with the ON duty fixed to the ON duty TO higher than the ON duty TS during the time of steady-state lighting of the excimer lamp.

2. The light source device according to claim 1, wherein the control circuit controls the switching element on and off so that the switching frequency (FS) at the time of starting to light the excimer lamp increases stepwise toward the switching frequency (FO) at the time of steady-state lighting of the excimer lamp.

3. The light source device according to claim 1, wherein the control circuit controls the switching elements on and off so that the ON-duty (TS) at the time of starting to light the excimer lamp increases stepwise toward the ON-duty (TO) at the time of steady-state lighting of the excimer lamp.

4. The light source device according to claim 1, wherein the excimer lamp comprises a light-emitting tube with a substantial rod shape and a pair of electrodes arranged in a ring shape at both ends of the light-emitting tube.

5. The light source device according to claim 1, wherein the excimer lamp emits ultraviolet light having a wavelength of 172 nm.

6. The light source device according to claim 5, wherein the excimer lamp comprises a light-emitting tube with a total length of 10 cm or less, and is a sterilizing/deodorizing lamp used in an enclosed space.

7. A sterilizing/deodorizing device comprising:
   an excimer lamp that emits ultraviolet light by dielectric-barrier discharge;
   a flyback-type lighting device that supplies power to the excimer lamp;
   a switching element equipped in the lighting device;
   a transformer to which the switching element is connected on the primary side and the excimer lamp is connected on the secondary side, the transformer being equipped in the lighting device; and
   a control circuit that supplies a drive signal to the switching element and that is equipped in the lighting device; wherein
   the control circuit controls the switching element on and off with the switching frequency fixed to the frequency FS and with the ON duty fixed to the ON duty TS for a predetermined time during the time of starting to light the excimer lamp,
   after the predetermined time elapsed, the control circuit controls the switching element on and off with the switching frequency increased from the frequency FS and the ON duty increased from the ON duty TS, and
   the control circuit controls the switching element on and off with the switching frequency fixed to the frequency FO higher than the frequency FS and with the ON duty fixed to the ON duty TO higher than the ON duty TS during the time of steady-state lighting of the excimer lamp.

* * * * *